United States Patent [19]

Wiesenfeldt et al.

[11] Patent Number: 5,428,140
[45] Date of Patent: Jun. 27, 1995

[54] PREPARATION OF PHENYLAZO- OR NAPHTHYLAZOBENZENES HAVING THIOETHER GROUPS

[75] Inventors: Matthias Wiesenfeldt, Mutterstadt; Bernd Siegel, Otterstadt; Manfred Patsch, Wachenheim, all of Germany

[73] Assignee: BASF Aktiengesellschaft, Ludwigshafen, Germany

[21] Appl. No.: 254,764

[22] Filed: Jun. 6, 1994

[30] Foreign Application Priority Data

Jun. 22, 1993 [DE] Germany .................... 43 20 661.1

[51] Int. Cl.⁶ ................ C09B 43/06; C09B 62/08; C09B 62/507
[52] U.S. Cl. ..................... 534/588; 534/612; 534/631; 534/634; 534/637; 534/643; 560/15
[58] Field of Search ........................ 534/588

[56] References Cited

U.S. PATENT DOCUMENTS

| | | | |
|---|---|---|---|
| 3,114,754 | 12/1963 | Lodge et al. | 534/588 X |
| 5,091,516 | 2/1992 | Siegel et al. | 534/612 |
| 5,182,371 | 1/1993 | Siegel et al. | 534/612 |
| 5,276,148 | 1/1994 | Siegel et al. | 534/605 |
| 5,278,291 | 1/1994 | Herd | 534/566 |

FOREIGN PATENT DOCUMENTS

| | | |
|---|---|---|
| 766771 | 6/1971 | Belgium ............... 534/588 |
| 0126265 | 11/1984 | European Pat. Off. |
| 0437699 | 7/1991 | European Pat. Off. |
| 0503385 | 9/1992 | European Pat. Off. |
| 0520241 | 12/1992 | European Pat. Off. |
| 0520241A2 | 12/1992 | European Pat. Off. |
| 4116785 | 11/1992 | Germany |

*Primary Examiner*—Mary C. Lee
*Assistant Examiner*—Fiona T. Powers
*Attorney, Agent, or Firm*—Oblon, Spivak, McClelland, Maier & Neustadt

[57] ABSTRACT

Reactive dyes of the formula

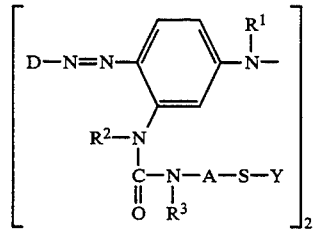

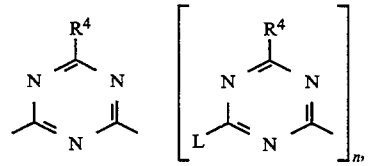

where
n is 0 or 1
$R^1$, $R^2$ and $R^3$ are in each case hydrogen, $C_1$-$C_4$-alkyl or phenyl,
$R^4$ is fluorine, chlorine, bromine, $C_1$-$C_4$-alkylsulfonyl, phenylsulfonyl or a radical of the formula

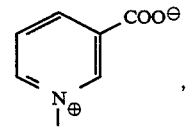

L is a bridge member,
A is unsubstitued or substituted $C_2$-$C_8$-alkylene,
Y is vinyl or a radical of the formula —$CH_2$—$CH_2$—Q, Q being a group which can be removed under alkaline reaction conditions, and
D is phenyl or naphthyl, it being possible for these radicals to be substituted,
and a process for preparing reactive dyes by oxidation of the abovementioned compounds are described.

5 Claims, No Drawings

PREPARATION OF PHENYLAZO- OR NAPHTHYLAZOBENZENES HAVING THIOETHER GROUPS

The present invention relates to novel compounds of the formula I

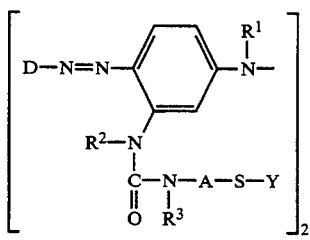 (I)

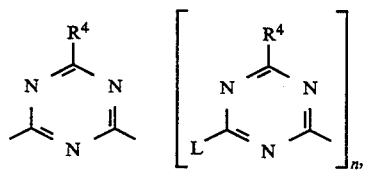

where n is 0 or 1

$R^1$, $R^2$ and $R^3$ are identical or different and independently of one another are in each case hydrogen, $C_1$–$C_4$-alkyl or phenyl, $R^4$ is fluorine, chlorine, bromine, $C_1$–$C_4$-alkylsulfonyl, phenylsulfonyl or a radical of the formula

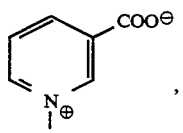

L is a bridge member,

A is a $C_2$–$C_8$-alkylene which may be interrupted by 1 to 3 ether oxygen atoms, imino groups or $C_1$–$C_4$-alkylimino groups, Y is vinyl or a radical of the formula —$CH_2$—$CH_2$—Q, Q being a group which can be removed under alkaline reaction conditions, and D is phenyl or naphthyl, it being possible for these radicals to be mono- or polysubstituted by hydroxysulfonyl, carboxyl, $C_1$–$C_4$-alkoxycarbonyl, cyano, $C_1$–$C_4$-alkyl, $C_1$–$C_4$-alkoxy, halogen, nitro or vinylsulfonyl, and a process for preparing reactive dyes by oxidation of the abovementioned compounds.

EP-A-520,241 describes the preparation of azo reactive dyes, starting from azo compounds which contain a 2-hydroxyethylthioether group, converting this into the 2-hydroxyethylsulfonyl group and then generating a sulfuric acid monoester group therefrom.

U.S. Pat. No. 5,182,371 discloses reactive dyes which are based on the molecular structure of the abovementioned compounds of the formula I, but which contain a sulfonyl group instead of the thioether group. These dyes have particularly favourable application properties, in particular high lightfastness, high tinctorial strength and good fixing behavior.

It is an object of the present invention to provide novel intermediates which are advantageously suitable for preparing these reactive dyes.

We have found that this object is achieved by the compounds of the formula I described in greater detail at the beginning.

In the present case, the novel compounds of the formula I are as a rule indicated in the form of a free acid. Of course, however, their salts are also additionally included.

Suitable salts in this case are metal or ammonium salts. Metal salts are in particular the lithium, sodium or potassium salts. Ammonium salts for the purpose of the invention are to be understood as meaning those salts which contain either unsubstituted or substituted ammonium cations. Substituted ammonium cations are eg. monoalkyl-, dialkyl-, trialkyl-, tetraalkyl- or benzyltrialkylammonium cations or those cations which are derived from nitrogen-containing 5- or 6-membered saturated heterocycles, such as pyrrolidinium, piperidinium, morpholinium, piperazinium or N-alkyl-piperazinium cations or their N-monoalkyl- or N,N-dialkyl-substituted products. Alkyl is in this case in general to be understood as meaning straight-chain or branched $C_1$–$C_{20}$-alkyl which can be substituted by hydroxyl groups and/or interrupted by ether oxygen atoms.

If substituted phenyl radicals occur in the abovementioned formula I, suitable substituents in this case can be, if not stated otherwise, eg. $C_1$–$C_4$-alkyl, $C_1$–$C_4$-haloalkyl, $C_1$–$C_4$-alkoxy, amino, $C_1$–$C_4$- mono- or dialkylamino, nitro, formyl, cyano, carboxyl or hydroxysulfonyl. As a rule, they contain 1 to 3 substituents.

The radicals $R^1$, $R^2$ and $R^3$ are eg. methyl, ethyl, propyl, isopropyl, butyl, isobutyl or sec-butyl.

The radicals $R^4$ are eg. methylsulfonyl, ethylsulfonyl, propylsulfonyl, isopropylsulfonyl or butylsulfonyl.

The radicals A are eg. —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$CH(CH_3)$—$CH_2$—, —$CH(CH_3)$—$CH(CH_3)$—, —$(CH_2)$—O—$(CH_2)_2$—, —$(CH_2)_2$—NH—$(CH_2)_2$—, —$(CH_2)_2$—N$(CH_3)$—$(CH_2)_2$—, —$(CH_2)_2$—O—$(CH_2)_2$—O—$(CH_2)_2$— or —$(CH_2)_2$—O—$(CH_2)_2$—O—$(CH_2)_2$—O—$(CH_2)_2$—.

Y in formula I is, inter alia, a group which can be removed under alkaline reaction conditions. Such groups are eg. chlorine, $OSO_3H$, $SSO_3H$, $OP(O)(OH)_2$, $C_1$–$C_4$-alkylsulfonyloxy, unsubstituted or substituted phenylsulfonyloxy, $C_1$–$C_4$-alkanoyloxy, $C_1$–$C_4$-dialkylamino,

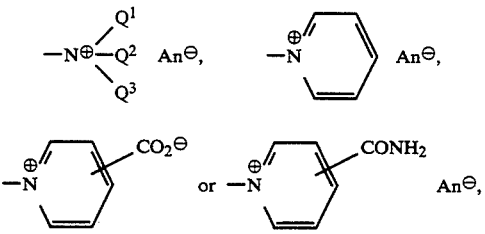

$Q^1$, $Q^2$ and $Q^3$ being identical or different and independently of one another in each case having the meaning of $C_1$–$C_4$-alkyl or benzyl and An$\ominus$ in each case having the meaning of an anion. (Suitable anions are eg. fluoride, chloride, bromide, iodide, mono-, di- or trichloroacetates, methanesulfonates, benzensulfonates or 2- or 4-toluenesulfonate.)

Preferred Y groups are $C_1$-$C_4$-alkanoyloxy, in particular acetoxy.

Suitable bridge members L comply eg. with the formula

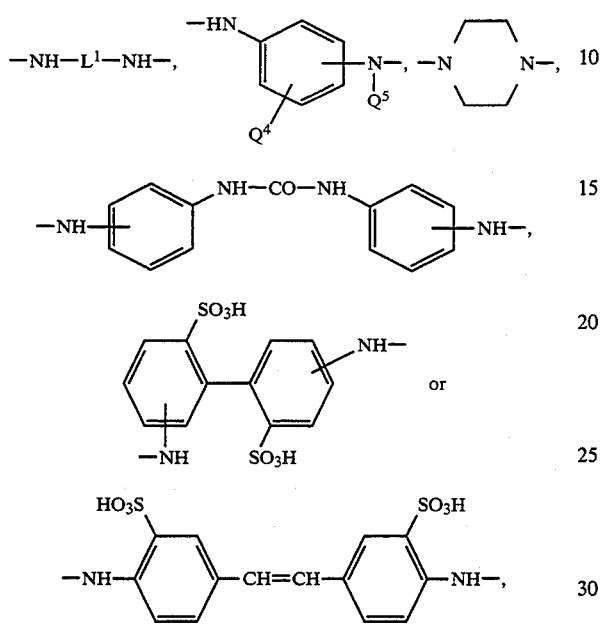

$L^1$ being $C_2$-$C_8$-alkylene, $Q^4$ being hydrogen or hydroxysulfonyl and $Q^5$ being hydrogen or $C_1$-$C_4$-alkyl.

Individual bridge members are eg. radicals of the formula

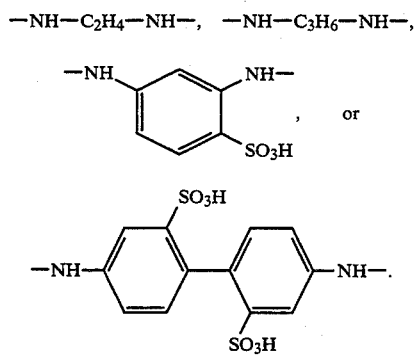

The radicals D are eg. 2,4-dihydroxysulfonylphenyl, 2,5-dihydroxysulfonylphenyl, 2,5-dihydroxysulfonyl-4-methylphenyl, 2,5-dihydroxysulfonyl-6-chlorophenyl, 3,6,8-trihydroxysulfonylnaphth-2-yl, 4,6,8-trihydroxysulfonylnaphth-2-yl, 1,5dihydroxysulfonylnaphth-2-yl or 1,6-dihydroxysulfonylnaphth-2-yl.

Preferred compounds of the formula I are those where $R^1$, $R^2$ and $R^3$ are in each case hydrogen,
$R^4$ is fluorine or chlorine,
A is $C_2$-$C_4$-alkylene, which may be interrupted by an ether oxygen, and
D is phenyl or naphthyl, these radicals being mono- to trisubstituted by hydroxysulfonyl.

Particularly preferred compounds of the formula I are those where

D is dihydroxysulfonylphenyl or trihydroxysulfonylnaphthyl.

Particularly preferred compounds of the formula I are furthermore those where, if n is 1, L is a radical of the formula $$-HN-\underset{Q^4}{\underset{|}{\bigcirc}}-\underset{Q^5}{\underset{|}{N-}},$$

where $Q^4$ and $Q^5$ in each case have the abovementioned meanings.

The novel compounds of the formula I are advantageously obtained if eg. an amine of the formula III $$D-NH_2 \qquad (III),$$

where D has the abovementioned meanings, is diazotized and coupled in a known manner with a phenylenediamine of the formula IV $$\text{(IV)}$$

where $R^1$, $R^2$, $R^3$, A and Y in each case have the abovementioned meanings.

The resulting azo compound of the formula V $$\text{(V)}$$

where D, $R^1$, $R^2$, $R^3$, A and Y in each case have the abovementioned meanings, can be reacted with trihalotriazine in a known manner. The reaction can be carried out in this case in a one-pot process or with isolation of the intermediates.

In order to obtain those compounds of the formula I in which n is zero, the reaction product can be reacted with further azo compound V.

In order to obtain those compounds of the formula I in which n is one, the product formed in the reaction with trihalotriazine can be reacted with a diamine of the formula VI $$H_2N-L-NH_2 \qquad (VI),$$

where L has the abovementioned meaning.

The phenylenediamines of the formula IV can be obtained by the method described in the earlier European Patent Application No. 93 115 520.4.

The novel compounds of the formula I are useful intermediates for preparing reactive dyes.

Accordingly, the present invention furthermore relates to a process for preparing reactive dyes of the formula II

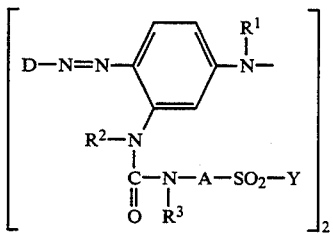
(II)

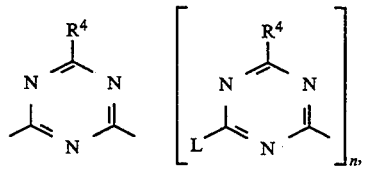

where n is 0 or 1

$R^1$, $R^2$ and $R^3$ are identical or different and independently of one another are in each case hydrogen, $C_1-C_4$-alkyl or phenyl, $R^4$ is fluorine, chlorine, bromine, $C_1-C_4$-alkylsulfonyl, phenylsulfonyl or a radical of the formula

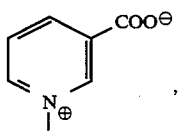

L is a bridge member,

A is $C_2-C_8$-alkylene which may be interrupted by 1 to 3 ether oxygen atoms, imino groups or $C_1-C_4$-alkylimino groups, Y is vinyl or a radical of the formula —$CH_2$—$CH_2$—Q, Q being a group which can be removed under alkaline reaction conditions, and D is phenyl or naphthyl, it being possible for these radicals to be mono- or polysubstituted by hydroxysulfonyl, carboxyl, $C_1-C_4$-alkoxycarbonyl, cyano, $C_1-C_4$-alkyl, $C_1-C_4$-alkoxy, halogen, nitro or vinylsulfonyl, which comprises treating compounds of the formula I

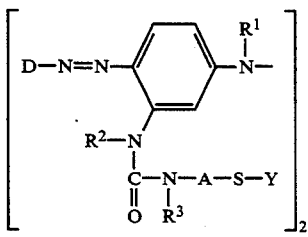
(I)

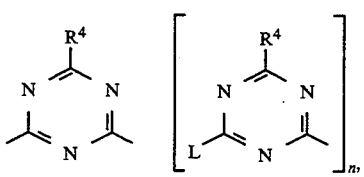

where n, $R^1$, $R^2$, $R^3$, $R^4$, L, A, Y and D in each case have the abovementioned meanings, in aqueous medium with an oxidant, if appropriate in the presence of catalysts, at from 0° to 110° C.

As far as the exemplary explanation of said radicals is concerned, reference may be made to the embodiments above.

Suitable oxidants are organic or inorganic oxidants, such as hydrogen peroxide, hydrogen peroxide-releasing compounds, organic hydroperoxides, percarboxylic acids, peroxomonosulfuric acid or its salts, in particular its alkali metal salts, peroxodisulfuric acid or its salts, in particular its alkali metal salts, alkali metal hypohalites, alkali metal permanganates, chromic acid or its salts, in particular its alkali metal salts, or nitric acid.

Suitable hydrogen peroxide-releasing compounds can be eg. alkali metal perborates or percarbonates.

Suitable organic hydroperoxides are eg. cumene hydroperoxide or alkyl hydroperoxides, in this case in particular tert-butyl hydroperoxide.

Suitable percarboxylic acids are eg. peracetic acid, m-chloroperbenzoic acid, magnesium bis(monoperoxyphthalate) hexahydrate or 1,12-dodecanediperacid.

The use of hydrogen peroxide as an oxidant is preferred.

As a rule, hydrogen peroxide is used in the process according to the invention as a 3 to 80% strength by weight aqueous hydrogen peroxide solution, 2–10 mol, preferably 2–4 mol, of aqueous hydrogen peroxide in general being used per mole of compound of the formula I.

Based on one part by weight of the compound of the formula I, a further 1 to 10 parts by weight of water are customarily additionally used as a reaction medium.

The process according to the invention can be carried out in the presence of catalysts. Suitable catalysts are eg. alkali metal tungstates, alkali metal molybdates or alkali metal vanadates, such as lithium tungstate, molybdate or vanadate, sodium tungstate, molybdate or vanadate or potassium tungstate, molybdate or vanadate.

As a rule, 0.001–0.1 part by weight of catalyst are used per part by weight of compound of the formula I.

The carrying out of the novel process in the presence of a catalyst is preferred, alkali metal tungstates, in particular sodium tungstate, being particularly emphasized as catalysts.

According to the invention, the oxidation of the thioether takes place at from 0° to 110° C., preferably 20° to 80° C. Customarily, oxidation is carried out under atmospheric pressure.

It is recommended to carry out the oxidation at a pH from 0 to 8, preferably 4 to 7.

The novel process, which can be carried out either continuously or batchwise, is expediently carried out by introducing the compound of the formula I together with water and, if desired, catalysts and setting the abovementioned pH range, if appropriate with the addition of base, eg. sodium hydrogencarbonate. The oxidant is then added at the abovementioned temperature. In general, the mixture is then stirred at from 20° to 80° C. for 0.5–5 hours. The resulting reaction mixture is then filtered and the filtrate containing the reactive dye II can be freed of solvent and dried.

The novel process can be carried out in a simple manner and yields the reactive dyes of the formula II in high yield and purity.

As already mentioned above, the reactive dyes of the formula II are useful products for dyeing or printing organic substrates containing hydroxyl groups or nitrogen atoms.

The following examples are intended to illustrate the invention in greater detail:

EXAMPLE 1 a) 462 g of a water-moist suction filter material (dry content: 70% by weight) of nitrophenylurea were treated with 700 g of xylene (isomer mixture) and 242 g of 2-aminoethyl-2'-hydroxyethyl sulfide and the mixture was heated to boiling. The xylene-water azeotrope boiling at 95° C. was removed by distillation and the reaction mixture was then heated to 140° C. to remove the residual xylene. After completion of the reaction (TLC checking), the mixture was cooled to 50° C. and 1 liter of water was added. The reaction mixture was adjusted to a pH of 11 using 20% strength by weight sodium hydroxide solution. The aqueous phase was then separated off and the water remaining in the organic phase was removed by azeotropic distillation. 6 g of 1-methylimidazole were added after cooling to 65° C. 277 g of acetic anhydride were added dropwise at this temperature. After cooling to 20° C., the resulting precipitate was filtered off with suction. 555 g of the compound of the formula

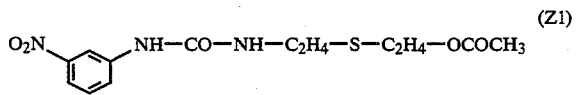
(Z1)

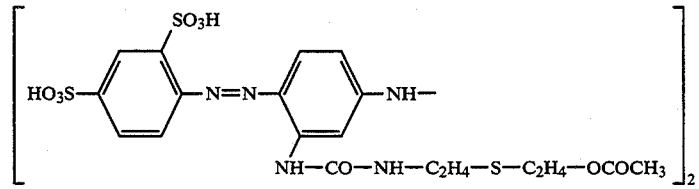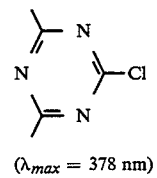

($\lambda_{max}$ = 378 nm)

were obtained. The following nitrophenylureas can be prepared in a similar manner:

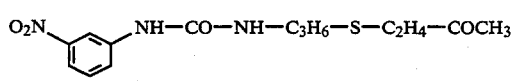
(Z2)

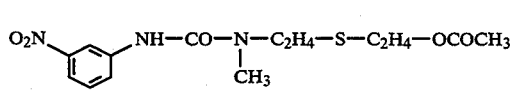
(Z3)

b) 565 g of the compound Z1 were suspended in 1800 ml of isobutanol. 130 g of Raney nickel were added to this mixture. It was then hydrogenated at 55°–60° C. in the course of 15 h by passing in hydrogen gas. After completion of the reaction (TLC checking), the catalyst was filtered off. The filtrate was concentrated under reduced pressure. The oil which remained crystallized after a short time. The crystals were filtered off with suction. 495 g of the compound of the formula

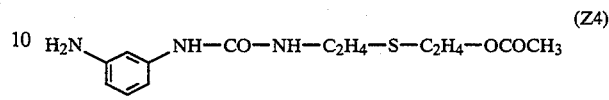
(Z4)

were obtained.

The following amino compounds can be prepared in a similar manner:

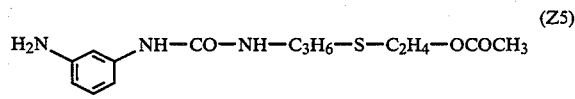
(Z5)

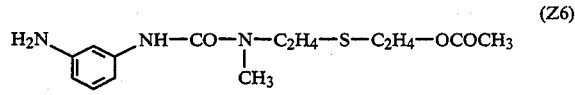
(Z6)

c) 101 g (0.4 mol) of aniline-2,4-disulfonic acid were diazotized in 400 ml of water containing hydrochloric acid and added to a suspension of 119 g (0.4 mol) of the compound Z4 in 500 ml of water. The coupling reaction was carried out at 0°–5° C. and a pH of 3 by addition of 2N potassium hydrogen carbonate solution.

d) The reaction solution described above was halved and the first half was condensed with 40.6 g (0.22 mol) of cyanuric chloride at 0°–5° C. and a pH of 5.5. The solution was then subjected to clarifying filtration and reacted with the second half of the coupling solution at 40°–50° C. and a pH of 5.5. After salting out, 204 g of the compound were obtained.

In order to obtain the compound described in d), the following procedure can also be used.

e) 254 g (1 mol) of aniline-2,4-disulfonic acid were diazotized with 320 ml of 23% strength by weight aqueous sodium nitrite solution in 1,000 g of ice/water mixture at 0°–5° C. 297 g (1.0 mol) of the compound Z4, suspended in 500 g of water, were then added and the coupling reaction was carried out at a pH of 3 with the aid of aqueous 1N sodium hydrogencarbonate solution. The resulting coupling solution was then treated with a mixture of 92 g (0.5 mol) of cyanuric chloride and 250 g of ice water. The 1st condensation step was then carried out at 0°–5° C. and a pH of 5.5, which was set by addition of sodium hydrogencarbonate solution. After 1 hour, the reaction mixture was heated to 40°-45° C. for the 2nd condensation step and a pH of 5.5 was maintained by means of sodium hydrogencarbonate solution. The resulting compound corresponds, as the free acid, to the compound described in Example 1d) and was isolated by salting out.

The compounds of the formula

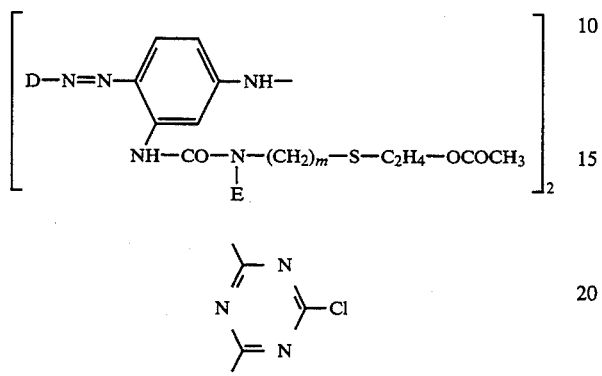

listed in Table 1 can be obtained in a similar manner.

TABLE 1

| Ex. No. | D | E | m |
|---|---|---|---|
| 2 | 2,5-disubstituted phenyl (SO₃H, HO₃S) | H | 2 |
| 3 | 2,5-disubstituted phenyl (SO₃H, HO₃S) | H | 3 |
| 4 | 2,5-disubstituted phenyl (SO₃H, HO₃S) | CH₃ | 2 |
| 5 | 2,5-disubstituted phenyl (SO₃H, HO₃S) | H | 3 |
| 6 | 2,5-disubstituted phenyl (SO₃H, HO₃S) | CH₃ | 2 |
| 7 | naphthyl (1-SO₃H, 5-SO₃H) | H | 2 |
| 8 | naphthyl (1-SO₃H, 5-SO₃H) | H | 3 |
| 9 | naphthyl (1-SO₃H, 5-SO₃H) | CH₃ | 2 |
| 10 | naphthyl (1-SO₃H, 3-HO₃S, 6-SO₃H) | H | 2 |
| 11 | naphthyl (1-SO₃H, 3-HO₃S, 6-SO₃H) | H | 3 |
| 12 | naphthyl (1-SO₃H, 3-HO₃S, 6-SO₃H) | CH₃ | 2 |
| 13 | naphthyl (1-SO₃H, 3-HO₃S, 5-SO₃H) | CH₃ | 2 |
| 14 | naphthyl (1-SO₃H, 3-HO₃S, 5-SO₃H) | H | 3 |
| 15 | naphthyl (1-SO₃H, 3-HO₃S, 5-SO₃H) | CH₃ | 2 |
| 16 | trisubstituted phenyl (SO₃H, CH₃, HO₃S) | H | 2 |

TABLE 1-continued

| Ex. No. | D | E | m |
|---|---|---|---|
| 17 | 2,5-disulfo-4-methylphenyl (SO₃H, CH₃, HO₃S) | H | 3 |
| 18 | 2-sulfo-4-methyl-5-sulfo (SO₃H, CH₃, HO₃S) | CH₃ | 2 |
| 19 | 4-chloro-3-sulfo-phenyl (Cl, HO₃S, SO₃H) | H | 2 |
| 20 | 4-chloro-3,5-disulfophenyl (Cl, HO₃S, SO₃H) | H | 3 |
| 21 | 4-chloro-3,5-disulfophenyl (Cl, HO₃S, SO₃H) | CH₃ | 2 |

EXAMPLE 22

0.4 mol of the coupling solution described in Example 1c) was condensed with 81.2 g (0.44 mol) of cyanuric chloride at 0°-5° C. and a pH of 5.5. The reaction solution was then subjected to clarifying filtration and treated with 21.6 g (0.2 mol) of para-phenylenediamine. To complete the reaction, the reaction mixture was heated to 40°-50° C. and a pH of 5.5 was maintained by addition of 2N sodium hydroxide solution. The compound could be isolated by spray drying and corresponds to the formula

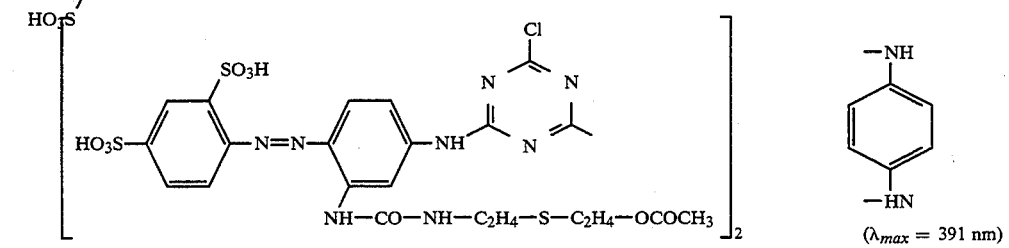

($\lambda_{max}$ = 391 nm)

The compounds of the formula

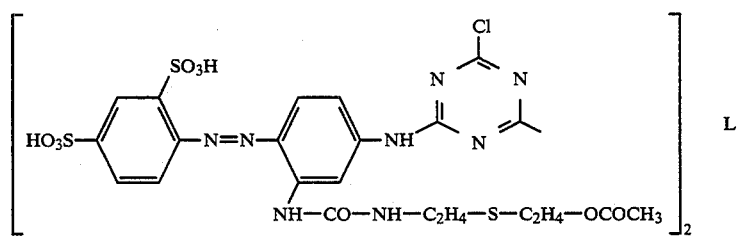

listed in Table 2 can be obtained in a similar manner.

TABLE 2

| Ex. No. | L |
|---|---|
| 23 | —HN—(1,3-phenylene)—NH— |
| 24 | —HN—C₂H₄—NH— |
| 25 | —HN—C₂H₄—NH— |
| 26 | piperazine-1,4-diyl (—N⌒N—) |
| 27 | —HN—(3-phenylene)—NHCNH—(3-phenylene)—NH— (with C=O) |

EXAMPLE 28

0.4 mol of the coupling solution described in Example 1c) was reacted with 81.2 g (0.44 mol) of cyanuric chloride at 0° to 5° C. and a pH of 5.5. The reaction solution was then subjected to clarifying filtration and treated with 37.6 g (0.2 mol) of 2,4-diaminobenzenesulfonic acid. To complete the reaction, the reaction mixture was heated to 40°-50° C. and a pH of 5.5 was maintained using 2N sodium hydroxide solution. The resulting compound was isolated by evaporating the reaction solution. It corresponds to the formula

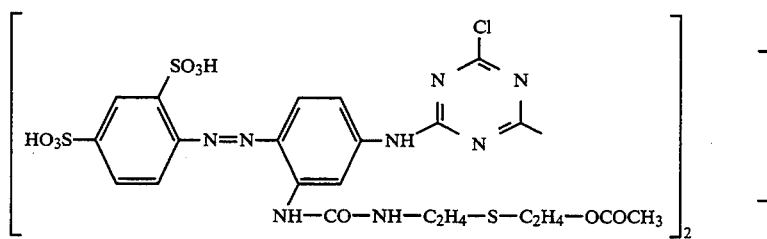

The compounds of the formula

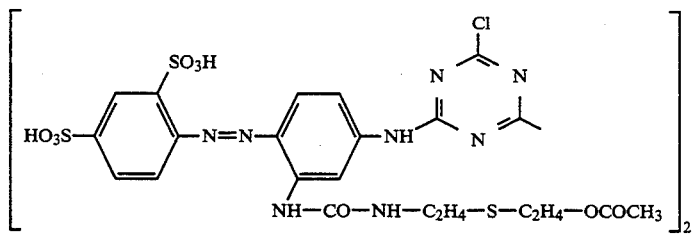

listed in Table 3 can be obtained in a similar manner.

TABLE 3

| Ex. No. | L |
|---|---|
| 29 | 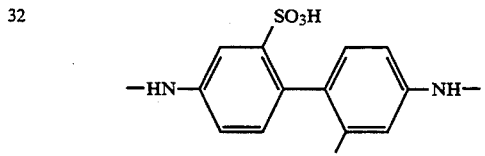 |
| 30 | 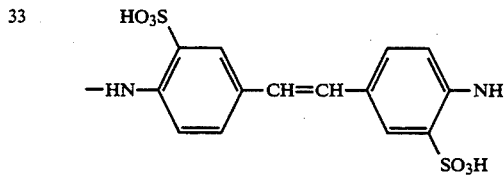 |
| 31 | |
| 32 | |
| 33 | |

TABLE 3-continued

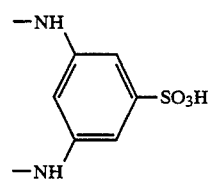

| Ex. No. | L |
|---|---|

EXAMPLE 34

100 g of the compound obtained according to Example 1d) were added to 250 ml of water. A pH of 6 was set using sodium hydrogencarbonate. 0.5 g of sodium tungstate was then added and 20 g of 30% strength by weight aqueous hydrogen peroxide solution were added dropwise. The resulting reaction mixture was stirred at 60° C. for 2 hours and filtered. The filtrate was concentrated under reduced pressure and the residue was dried. 98 g of the reactive dye of the formula

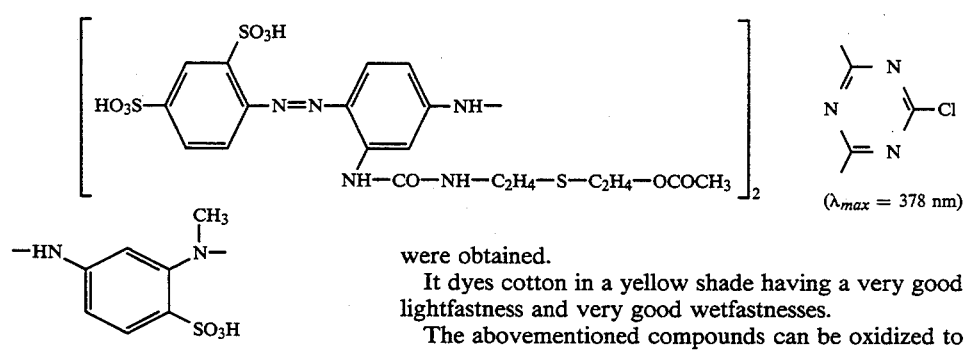

($\lambda_{max}$ = 378 nm)

were obtained.

It dyes cotton in a yellow shade having a very good lightfastness and very good wetfastnesses.

The abovementioned compounds can be oxidized to the corresponding reactive dyes in a similar manner.

We claim:

1. A process for preparing reactive dyes of the formula II

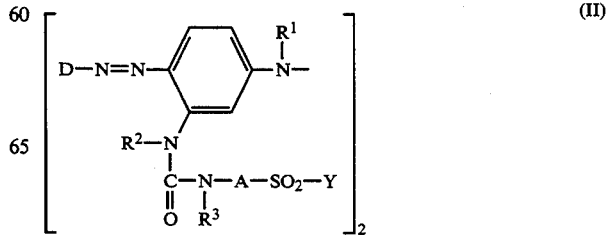

-continued

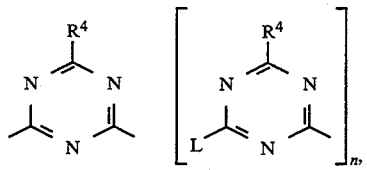

where n is 0 or 1

R¹, R² and R³ are identical or different and independently of one another are in each case hydrogen, $C_1$-$C_4$-alkyl or phenyl, R⁴ is fluorine, chlorine, bromine, $C_1$-$C_4$-alkylsulfonyl, phenylsulfonyl or a radical of the formula

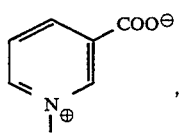

L is a bridge member,

A is $C_2$-$C_8$-alkylene which may be interrupted by 1 to 3 ether oxygen atoms, imino groups or $C_1$-$C_4$-alkylimino groups, Y is vinyl or a radical of the formula —CH$_2$—CH$_2$—Q, Q being a group which can be removed under alkaline reaction conditions, and D is phenyl or naphthyl, it being possible for these radicals to be mono- or polysubstituted by hydroxysulfonyl carboxyl, $C_1$-$C_4$- alkoxycarbonyl, cyano, $C_1$-$C_4$-alkyl, $C_1$-$C_4$-alkoxy, halogen, nitro or vinylsulfonyl, which comprises treating compounds of the formula I

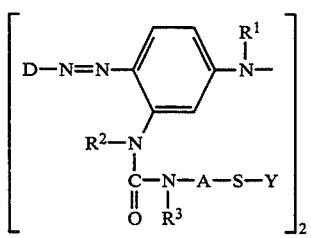

(I)

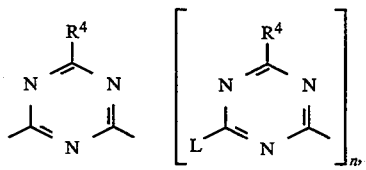

where n, R¹, R², R³, R⁴, L, A, Y and D in each case have the abovementioned meanings, in aqueous medium at a pH of from 4 to 7 with an oxidant, optionally in the presence of catalysts, at from 0° to 110° C.

2. The process as claimed in claim 1, wherein the oxidant used is hydrogen peroxide.

3. The process as claimed in claim 1, wherein L is selected from the group consisting of

—NH—L¹—NH—,

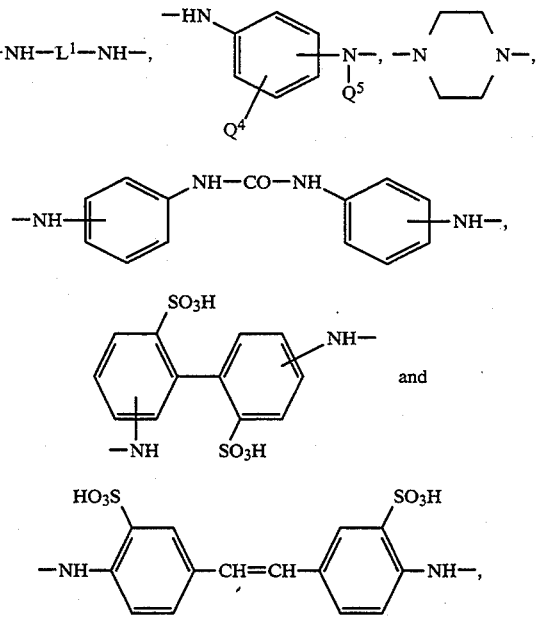

where L¹ is $C_2$-$C_8$-alkylene, Q⁴ is hydrogen or hydroxysulfonyl and Q⁵ is hydrogen or $C_1$-$C_4$-alkyl.

4. The process as claimed in claim 3, wherein L is selected from the group consisting of

—NH—C$_2$H$_4$—NH—, —NH—C$_3$H$_6$—NH—,

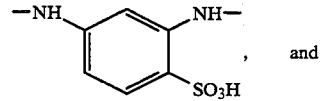

and

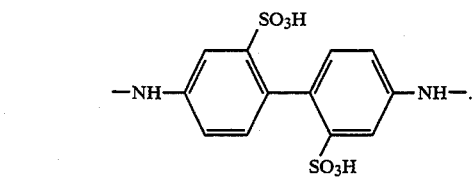

5. The process as claimed in claim 3, wherein said L is a radical of the formula

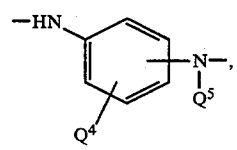

* * * * *